(12) United States Patent (10) Patent No.: US 12,636,194 B2
Wu (45) Date of Patent: May 26, 2026

(54) EAR MUFF AND EAR MUFF ASSEMBLY

(71) Applicant: TECMEN ELECTRONICS CO., LTD, Nanjing (CN)

(72) Inventor: Ziqian Wu, Nanjing (CN)

(73) Assignee: TECMEN ELECTRONICS CO., LTD, Nanjing (CN)

( * ) Notice: Subject to any disclaimer, the term of this patent is extended or adjusted under 35 U.S.C. 154(b) by 289 days.

(21) Appl. No.: 18/554,619

(22) PCT Filed: Apr. 7, 2022

(86) PCT No.: PCT/CN2022/085453
§ 371 (c)(1),
(2) Date: Oct. 9, 2023

(87) PCT Pub. No.: WO2022/214010
PCT Pub. Date: Oct. 13, 2022

(65) Prior Publication Data
US 2024/0207100 A1 Jun. 27, 2024

(30) Foreign Application Priority Data

Apr. 9, 2021 (CN) .......................... 202110381688.2
Apr. 9, 2021 (CN) .......................... 202120721250.X

(51) Int. Cl.
*A61F 11/14* (2006.01)
*H04R 5/033* (2006.01)

(52) U.S. Cl.
CPC ................................... *A61F 11/145* (2022.01)

(58) Field of Classification Search
CPC ........ A61F 11/14; A61F 11/145; A61F 11/06;
H04R 1/02; H04R 1/10; H04R 1/105;
(Continued)

(56) References Cited

U.S. PATENT DOCUMENTS 2,054,907 A * 9/1936 Mollet ...................... E05C 7/06
292/99
2,235,372 A * 3/1941 Kalbitz ................ H04R 1/1066
381/379
(Continued)

FOREIGN PATENT DOCUMENTS

CN 1157202 A 8/1997
CN 1199589 A 11/1998
(Continued)

OTHER PUBLICATIONS

IP Australia, Examination Report No. 1 issued Jul. 18, 2024 regarding Application No. 2022253837, 6 pages.
(Continued)

*Primary Examiner* — Edgardo San Martin

(57) ABSTRACT

The present application discloses an ear muff and an ear muff assembly. The ear muff comprises a housing base in which an acoustic cavity for noise attenuation is formed and a chamber for receiving an electronic device is formed; an outer cover for covering the chamber; and a locking structure acting between the outer cover and the housing base, so as to achieve a releasable connection between the outer cover and the housing base, characterized in that the locking structure comprises: a first locking component securely provided on the outer cover to selectively engage the housing base; a second locking component pivotably provided on the outer cover and spaced apart from the first locking component, the second locking component being configured to be pivotable between a locking position, in which the outer cover is able to be locked together with the housing base due to the locking structure, and an unlocking position in which the outer cover is able to be released from the housing base; and a force exerting element provided between the second locking component and the outer cover by which force exerting element a force is always applied to
(Continued)

the second locking component, tending to return the second locking component from the unlocking position to the locking position.

20 Claims, 5 Drawing Sheets

(58) Field of Classification Search
CPC .. H04R 1/1008; H04R 1/1041; H04R 1/1083; H04R 1/1058; H04R 1/1066; H04R 1/1091; H04R 1/1075; H04R 5/033; H04R 5/0335; H04R 2201/10; H04R 2201/103; H04R 2201/105
See application file for complete search history.

(56) References Cited

U.S. PATENT DOCUMENTS

| | | | | |
|---|---|---|---|---|
| 4,428,013 | A * | 1/1984 | Posso | G11B 17/03 |
| 4,532,194 | A * | 7/1985 | Liautaud | H01M 50/213 |
| | | | | 429/163 |
| 5,681,214 | A | 10/1997 | Kleider et al. | |
| 5,864,928 | A | 2/1999 | Matsushima | |
| 6,189,938 | B1 * | 2/2001 | Nakadaira | E05C 19/06 |
| | | | | 292/87 |
| 6,394,300 | B1 * | 5/2002 | Bosy | H01M 50/213 |
| | | | | 429/97 |
| 6,490,436 | B1 * | 12/2002 | Kaiwa | H04M 1/0262 |
| | | | | 455/575.1 |
| 7,855,008 | B2 * | 12/2010 | Hakunti | H04M 1/0262 |
| | | | | 429/96 |
| 7,892,668 | B2 * | 2/2011 | Choi | H04B 1/3883 |
| | | | | 429/97 |
| 8,189,801 | B2 * | 5/2012 | Heringslack | A61F 11/14 |
| | | | | 381/71.7 |
| 8,243,943 | B2 | 8/2012 | Nordin et al. | |
| 8,249,679 | B2 * | 8/2012 | Cui | G06F 1/181 |
| | | | | 455/575.8 |
| 8,953,815 | B2 * | 2/2015 | Shinozaki | H04R 1/1091 |
| | | | | 381/384 |
| 9,445,182 | B2 * | 9/2016 | Pizzaro | H04R 1/1008 |
| 9,510,079 | B1 | 11/2016 | Pastorino | |
| 9,866,944 | B1 | 1/2018 | Wright | |
| 10,149,033 | B2 | 12/2018 | Karacal | |
| 10,154,335 | B1 * | 12/2018 | Hoang | H04R 1/1008 |
| 10,172,742 | B2 | 1/2019 | Fletcher et al. | |
| 10,187,715 | B2 * | 1/2019 | Karacal | H04R 1/1008 |
| 10,349,162 | B2 * | 7/2019 | Ohlander | H04R 1/1008 |
| 10,567,860 | B2 * | 2/2020 | Han | H04R 1/1041 |
| 2007/0226877 | A1 | 10/2007 | Hansson et al. | |
| 2008/0192973 | A1 | 8/2008 | Heringslack | |
| 2011/0142249 | A1 | 6/2011 | Shinozaki | |
| 2015/0222980 | A1 | 8/2015 | Pizzaro et al. | |
| 2018/0176673 | A1 | 6/2018 | Madsen et al. | |
| 2018/0184194 | A1 | 6/2018 | Ohlander et al. | |
| 2018/0220218 | A1 | 8/2018 | Karacal | |
| 2019/0373351 | A1 | 12/2019 | Han | |
| 2021/0100689 | A1 | 4/2021 | Himuro et al. | |
| 2025/0195276 | A1 * | 6/2025 | Wu | A61F 11/14 |

FOREIGN PATENT DOCUMENTS

| | | | | |
|---|---|---|---|---|
| CN | 101076306 | A | 11/2007 | |
| CN | 101166489 | A | 4/2008 | |
| CN | 204785421 | U | 11/2015 | |
| CN | 108210167 | A | 6/2018 | |
| CN | 108235166 | A | 6/2018 | |
| CN | 110249635 | A | 9/2019 | |
| CN | 110254215 | A * | 9/2019 | A62C 3/07 |
| CN | 210020900 | U | 2/2020 | |
| CN | 112972116 | A | 6/2021 | |
| CN | 214967652 | U | 12/2021 | |
| EP | 0235548 | A1 * | 9/1987 | E01F 13/123 |
| FR | 3090455 | A1 * | 6/2020 | B29C 70/78 |
| WO | 2006118515 | A1 | 11/2006 | |

OTHER PUBLICATIONS

Chinese National Intellectual Property Administration, Office Action issued Jul. 27, 2024 regarding Application No. 202110381688.2, 16 pages.

Extended European Search Report issued Nov. 12, 2024 regarding Application No. 22784076.6, 7 pages.

International Search Report and Written Opinion issued Jul. 6, 2022 regarding International Application No. PCT/CN2022/085453 10 pages.

* cited by examiner

100

100

EAR MUFF AND EAR MUFF ASSEMBLY

CROSS REFERENCE TO RELATED APPLICATIONS

This application is a 371 National Stage of International Application No. PCT/CN2022/085453, filed Apr. 7, 2022, which claims priority to Chinese Patent Application No. 202110381688.2 filed on Apr. 9, 2021 and Chinese Patent Application No. 202120721250.X filed on Apr. 9, 2021, the disclosures of which are herein incorporated by reference in their entirety.

TECHNICAL FIELD

The present application generally relates to an ear muff assembly for use on an industrial site, especially to an ear muff of the assembly.

BACKGROUND

Various kinds of noise interferences exist on the industrial site. Therefore, an operator if working on the industrial site may have to wear an ear muff or an ear muff assembly on his/her head so as to prevent his/her hearing from being irremediably damaged. Moreover, the ear muff assembly is usually equipped with a microphone and a headset, such that the level of heard noise on the industrial site could be reduced, voice of some persons in a noisy scene could be picked up and be transmitted to other persons who wear the ear muff or ear muff assembly such that they could be in effective communication with each other at any time.

An ear muff can generally cover an entire ear of a person such that on-site noise over most frequency ranges could be shielded by the physical mechanical structural design of a housing of the ear muff. Besides, in order that electronic devices such as the headset, relevant control circuits or the like can be operated, a battery for example a rechargeable battery need be equipped in the housing of the ear muff as a power source for the electronic devices. Therefore, it is necessary to design at least a part of the housing of the ear muff to be releasable such that if desired the battery could be removed from the housing and replaced with a new one or the circuits in the housing of the ear muff could be serviced.

Usually, the same one ear muff assembly is most likely worn by different operators on site. Each of them might have different working habits or experiences. Therefore, it is desirable to provide a locking structure for the housing of the ear muff, by which locking structure the housing could be reliably locked and readily openable.

SUMMARY

In order to solve the above issues, the present application is aimed at proposing a novel designed locking structure which can be used in an ear muff's housing such that the ear muff's housing can be readily and reliably locked or unlocked on site.

According to an aspect of the present application, an ear muff is proposed, which comprises: a housing base in which an acoustic cavity for noise attenuation is formed and a chamber for receiving an electronic device is formed; an outer cover for at least covering the chamber; and a locking structure acting between the outer cover and the housing base, so as to achieve a releasable connection between the outer cover and the housing base, characterized in that the locking structure comprises: a first locking component securely provided on the outer cover to selectively engage the housing base; a second locking component pivotably provided on the outer cover and spaced apart from the first locking component, the second locking component being configured to be pivotable between a locking position, in which the outer cover is able to be locked together with the housing base due to the locking structure, and an unlocking position in which the outer cover is able to be released from the housing base; and a force exerting element provided between the second locking component and the outer cover by which force exerting element a force is always applied to the second locking component, tending to return the second locking component from the unlocking position to the locking position. According to the present application, the connection or disconnection between the outer cover and the housing base can be achieved by pivoting the second locking component of the locking structure. Therefore, it will be more convenient for a user to detach or assemble the ear muff. Moreover, because of the existence of the force exerting element, the outer cover can be reliably locked onto the housing base and the second locking component can be automatically reset.

In an embodiment, the first locking component is configured to engage both of the second locking component in its locking position and the housing base so as to lock the outer cover to the housing base.

In an embodiment, the force exerting element is located in an installation space which is defined between the second locking component and the outer cover and whose volume is able to change as the second locking component is pivoted.

In an embodiment, the first locking component comprises or is a projection formed on a circumferentially extending edge of the outer cover, and a slot is formed in a peripheral region of the housing base to engage the projection.

In an embodiment, a locking receptacle is formed in the peripheral region of the housing base to at least partially receive the second locking component.

In an embodiment, the first locking component is spaced apart from the second locking component along a diameter of the outer cover. It is noted that the term "diameter" does not means that the outer cover has to be circular or elliptical, and can be construed as the maximum extent or distance measured between the first and second locking components, viewed in a cross-section passing through the outer cover perpendicular to a thickness direction of the housing base.

In an embodiment, the second locking component comprises a lockable portion which is configured to together with the outer cover define the installation space, and an actuatable portion, wherein when the outer cover is locked to the housing base, the lockable portion is at least partially located in the locking receptacle and the actuatable portion is exposed. By a user's finger moving the actuatable portion, the second locking component is enabled to be pivoted. In comparison to a case in which the locking component can be linearly movable only, the present application can be used to achieve convenient operation of the locking structure.

In an embodiment, the lockable portion comprises at least an arc-shaped edge, at least one arc-shaped ridge is formed in the locking receptacle, the arc-shaped edge is formed to follow the arc-shaped ridge such that when the lockable portion is pivoted in the locking receptacle, the arc-shaped edge is pivoted around or moved along the arc-shaped ridge. The design of the arc-shaped edge and the arc-shaped ridge can be helpful to guide the pivoting movement of the actuatable portion in the locking receptacle, and prevent the actuatable portion from accidently escaping out of the locking receptacle. Therefore, the reliability of the locking structure can be improved according to the present application.

In an embodiment, the arc-shaped edge is configured to in the locking position apply a force to the arc-shaped ridge so as to resist the lockable portion leaving the locking receptacle.

In an embodiment, the force exerting element is configured as a torsional spring which is provided with a spiral spring segment and two spring arms extending from both ends of the spiral spring segment respectively. In an embodiment, the central axis of the spiral spring segment coincides with the pivotal axis of the second locking component or is parallel to the same.

In an embodiment, in the installation space, one of the two spring arms is in contact with the second locking component and the other is in contact with the outer cover.

In an embodiment, the force exerting element is configured as a pair of magnets, a first magnet of the pair of magnets is located on the lockable portion and a second magnet of the pair of magnets is located on the outer cover, and a side of the first magnet and a side of the second magnet opposing each other have the same magnetism.

In an embodiment, the electronic device comprises an electronic device for noise attenuation.

According to another aspect of the present application, an ear muff assembly is proposed, which comprises: a headband; and a pair of ear muffs which are releasably connected to opposing ends of the headband respectively, wherein one or each ear muff of the pair of ear muffs is an ear muff as above mentioned.

Using the inventive technical measures, a user can conveniently and reliably lock the outer cover onto the housing base of the ear muff, such that the electronic device in the ear muff can be safely protected. Besides, if desired, it will be convenient for the user to detach the outer cover and make necessary servicing for or replacement for the electronic device.

BRIEF DESCRIPTION OF THE DRAWINGS

The principle and other aspects of the present application would be well understood through the following detailed description in combination of the attached drawings. In the drawings.

DETAILED DESCRIPTION

Figure 1:
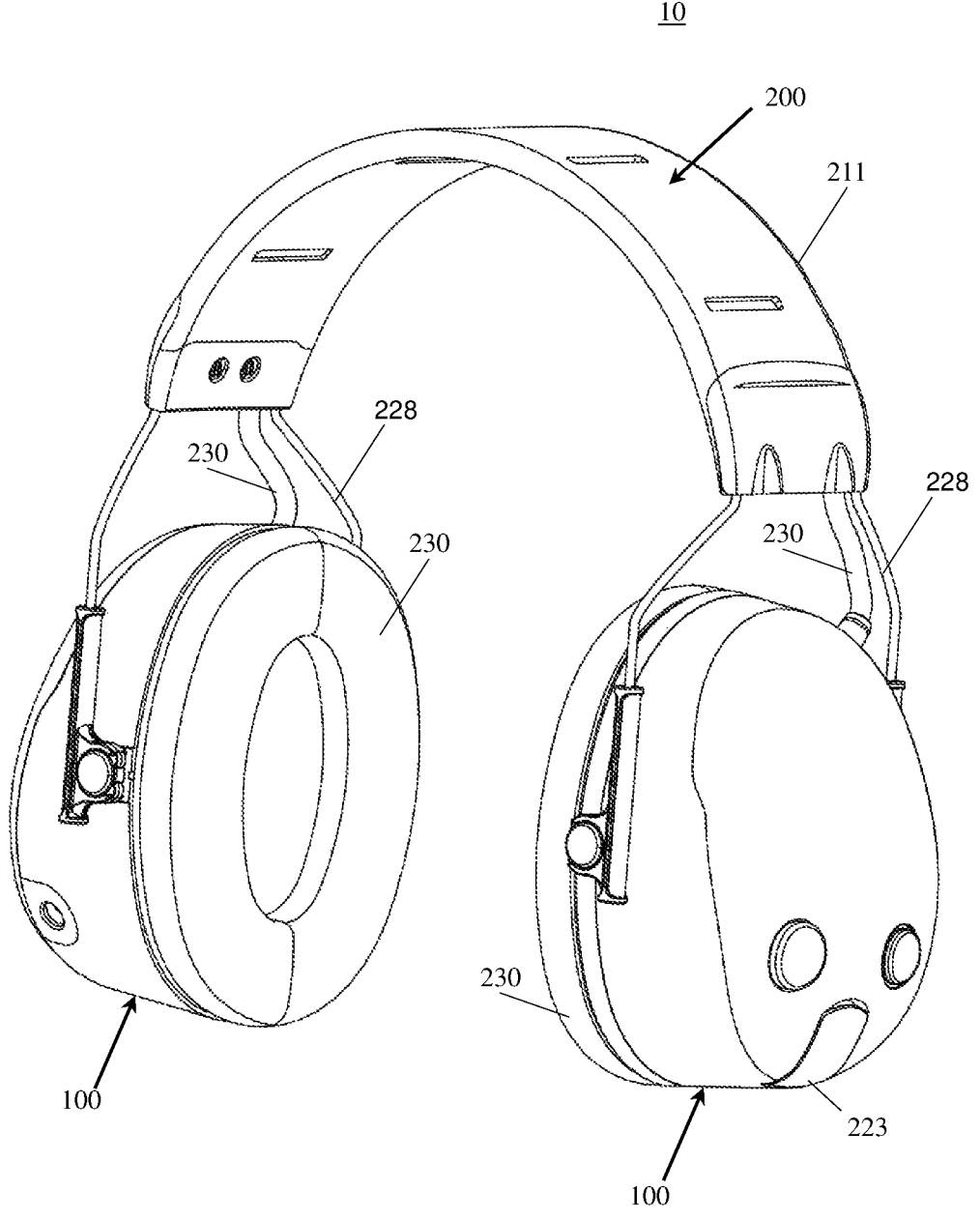
FIG. 1 is a perspective view schematically illustrating an ear muff assembly according to an embodiment of the present application.

In the drawings of the present application, those feature having similar configurations or functions are represented by the same reference numerals respectively.

FIG. 1 schematically shows an example of an ear muff assembly 10 of the present application. The ear muff assembly 10 generally comprises a pair of ear muffs 100 and a headband 200 connecting them. The headband 200 is configured to be worn on a user's head and to have opposite ends which can be releasably connected to the pair of ear muffs 100 respectively. One or each of the pair of ear muffs 100 is able to be provided with electronic devices such as a Bluetooth module, a headset, a control circuit, a battery or the like. Therefore, a removable outer cover is provided (as mentioned below) for the ear muff(s) such that it will be convenient to replace the battery with a new one or have the relevant electronic devices serviced. For example, the headband 200 can generally comprise a flexible curved band section 211 for contacting the user's head and a bracket, especially a metal bracket 228, extending from each of both opposite ends of the flexible curved band section 211. Moreover, a conductive cable 230 is configured to extend at least partially through the headband 200 by which conductive cable the two ear muffs 100 can be electrically connected to each other. Each of the ear muffs 100 is connected to the headband 200, especially to the respective bracket or metal bracket 228 of the headband in such a way that the ear muffs 100 are pivotable relative to the headband 200. In this way, it is convenient to adjust the ear muffs 100 relative to the headband so that the ear muff assembly can adopt for the user's head contour. Especially, the brackets or metal brackets 228 can be configured to be stretchable relative to the flexible curved band section 211 so as to adopt for the user's head contour or the flexible curved band section 211 itself can be configured to be telescopic and adjustable along its lengthwise direction.

An ear muff 100 according to an embodiment of the present application will be explained below with respect to FIGS. 2 to 5B. It is appreciated by a person skilled in the art that the ear muff 100 explained here can refer to any one or each of the ear muffs of the ear muff assembly 10.

Figure 2:
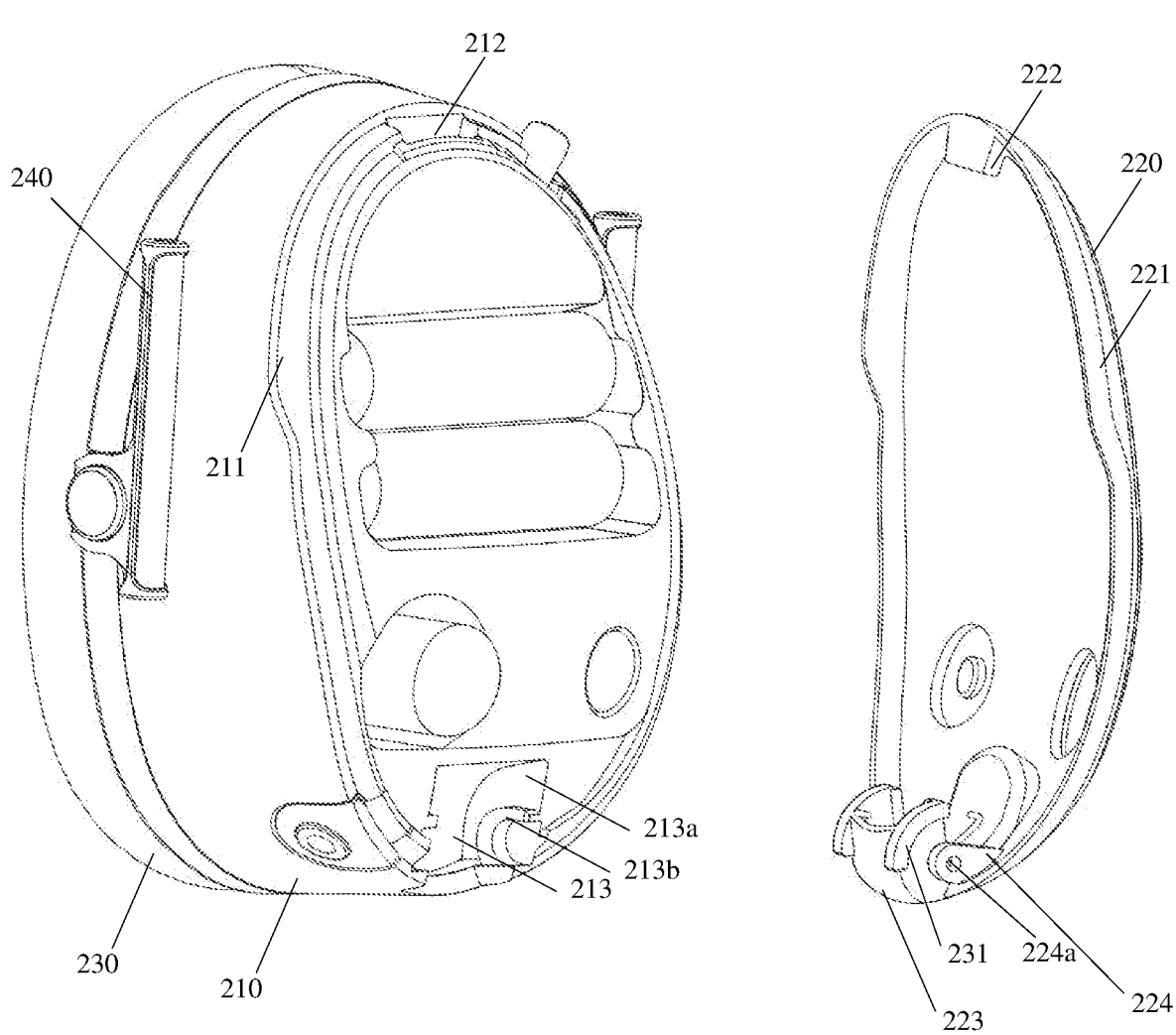
FIG. 2 is an exploded and perspective view schematically illustrating an ear muff according to an embodiment of the present application, wherein the ear muff can be fitted as a part of the ear muff assembly of FIG. 1, an outer cover as a part of the ear muff's housing is separated from a base of the housing, and a locking structure is in a locking state.

FIG. 2 is an exploded and perspective view schematically illustrating the ear muff 100 according to the embodiment of the present application. The ear muff 100 can comprise a housing base 210, an outer cover 220 installable on a side of the housing base 210 departing from a user's head when the ear muff is used, and an ear pad installable on a side of the housing base 210 facing the user's head when the ear muff is used. For clarity, it is shown by FIG. 2 that the outer cover 220 has been detached from the housing base 210 and a side of the outer cover 220 facing the housing base 210 when the outer cover is installed can be observed.

The housing base 210 can be for example made of a plastic material. In an interior of the housing base, an acoustic cavity can be formed so as to attenuate noise from the outside, and electronic devices such as a Bluetooth module, a headset, a sound pick-up, a control circuit, a battery or the like can be received. Here, the electronic devices include but are not limited by an electronic device for noise attenuation. Therefore, in order to meet requirements of servicing the electronic devices and/or replacing them with new ones respectively, the outer cover 220 is generally configured to be disposed on the side of the housing base 210 departing from the user's head when the ear muff or ear muff assembly is used/worn. In this way, the electronic devices can be sheltered from external force harm on the working site.

The ear pad 230 is installed on the side of the housing base 210 opposing the outer cover 220, and is configured to contact the user's head, especially his/her ear or the skin or issue around the ear. Therefore, the ear pad 230 is substantially shaped to be an annular and has a foamed or sponge body. A pair of pivotal connection features 240 are provided on a peripheral region of the housing base 210 such that they are respectively connectable to the bracket or metal bracket 228. More particularly, the bracket or metal bracket 228 is adjustable by moving it relative to the pivotal connection features 240.

Figure 3:
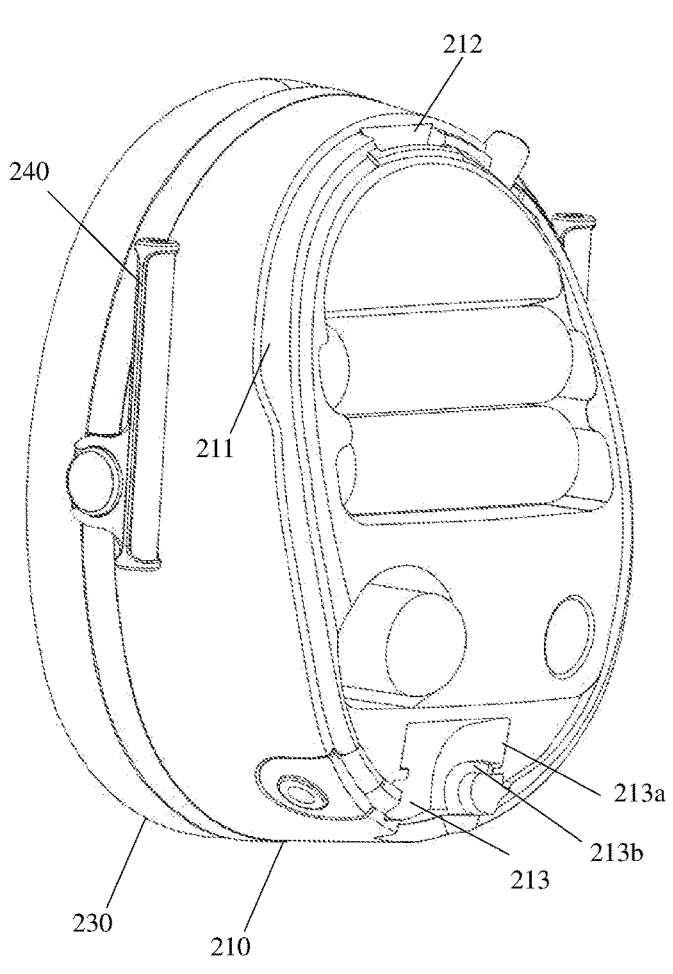
FIG. 3 is an exploded and perspective view schematically illustrating the ear muff of FIG. 2 but the locking structure is in an unlocking state.
Figure 3:
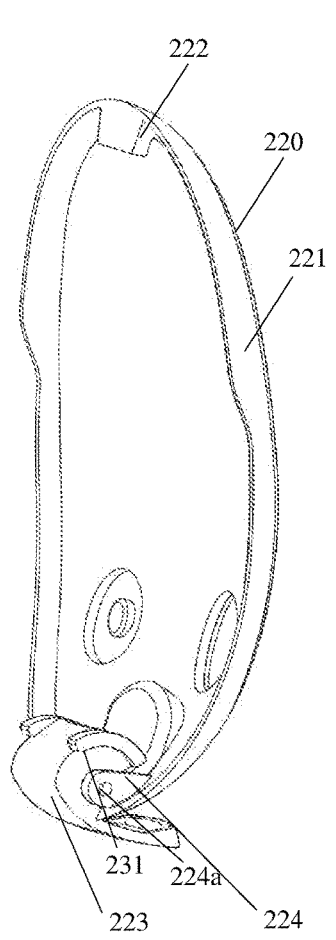

For example, the outer cover 220 can also be made of a plastic material. As shown by FIGS. 2 and 3, a chamber can be formed in the side of the housing base 210 departing from the user's head, when the ear muff or ear muff assembly is used, so as to receive the electronic devices. The outer cover 220 is at least configured to achieve coverage of the chamber. In an embodiment of the present application, the chamber is for example configured to receive at least two AAA-type batteries. Of course, it shall be understood by a person skilled in the art that the chamber can be configured to receive any other (not shown or not described here) electronic devices. A circumferentially extending undercut 211 is formed around the housing base 210. Correspondingly, a circumferentially extending edge 221 is formed along a periphery of a side of the outer cover 220 facing the housing base 210. In an optional embodiment, the circumferentially extending undercut 211 can be formed continuously or intermittently around the housing base 210, and the circumferential extending edge 221 can be formed continuously or intermittently along the side periphery of the outer cover 220. When the outer cover 220 is in tight contact with the housing base 210, the circumferentially extending edge 221 is just able to engage the circumferentially extending undercut 211 so as to achieve a seal therebetween. Therefore, the electronic devices received in the housing base 210 and surrounded by the outer cover are prevented from being damaged. In a preferred embodiment, an elastic seal strip is provided on the circumferentially extending edge 221 and/or the circumferentially extending undercut 211 so as to guarantee an air-proof or water-proof connection between the outer cover 220 and the housing base 210.

At least one slot 212 is formed in the peripheral region of the housing base 210. For instance, the at least one slot 212 is able to be in communication with the circumferentially extending undercut 212. Moreover, at least one projection 222 is formed on the side periphery of the outer cover 220, especially on the circumferentially extending edge 221 of the outer cover 220. In an embodiment of the present application, the slot 212 is for example configured to extend, starting from the circumferentially extending undercut 211, radially towards a center of the housing base 210, especially towards its geometrical center, as shown by FIGS. 4A to 4D. Similarly, the projection 222 can be for example configured to extend, starting from the circumferentially extending edge 221, substantially radially towards a center of the outer cover 220, especially towards its geometrical center. Therefore, when the circumferentially extending edge 221 engages the circumferentially extending undercut 211, the projection 222 can protrude into the slot 212, providing some degree of locking between the outer cover 220 and the housing base 210.

A locking receptacle 213 is formed in the peripheral region of the housing base 210 substantially at a location radially opposing the at least one slot 212. The locking receptacle 213 is configured to at least partially receive a pivotable locking component 223 provided on the outer cover 220 and explained below. The locking receptacle 213 is formed inwardly along a thickness direction of the housing base 210. In the context of the present application, the thickness direction of the housing base concerned refers to a direction substantially along the coronal direction of a user who is wearing the ear muff assembly 10 or the ear muff 100, or to a direction substantially parallel to the coronal direction of the user.

As shown by FIGS. 2 and 3, two opposing walls 213a (only one of them is visible in the drawings) are formed in the locking receptacle 213. Moreover, two opposing arc-shaped ridges 213b (only one of them is visible in the drawings) are formed on the two opposing walls 213a respectively. Each of the two arc-shaped ridges 213b extends outwards from the respective one of the walls 213a in a similar or the same trajectory shape. Moreover, the two arc-shaped ridges 213b extend in opposing directions.

Viewed externally, the outer cover 220 is provided with a section 225 recessed towards the housing base 210. That is to say, the section 225 protrudes inwardly from a side of the outer cover 220 facing the housing base 210. Two lugs 224 (only one of them is visible in FIGS. 2 and 3) spaced apart from each other are formed on the side of the outer cover 220 facing the housing base 210. The two lugs 224 can be located at or adjacent to two lateral sides of the section 225. In the context of the present application, the term "lateral" can relate to a direction of a part or an assembly, when it is installed in place as a part of the ear muff assembly 100 or ear muff 10 and when the muff assembly 100 or ear muff 10 is worn by a user, substantially along the user's coronal direction or substantially parallel to the user's coronal direction.

The pivotable locking component 223 is configured to be pivotally installed between the two lugs 224, such that the locking component 223 has a lockable portion 223a (i.e., a first portion) located at the side of the outer cover 220 facing the housing base 210 and an actuatable portion 223b (i.e., a second portion) located at a side of the outer cover 220 departing from the housing base 210. The locking component 223 can be for example made of a plastic material as an integral piece. As an example, a pair of pivotal pins opposite to each other are formed on the locking component 223. For instance, the pivotal pins can be formed between the lockable portion 223a and the actuatable portion 223b. Therefore, by clamping the locking component 223, especially its lockable portion 223a between the two lugs 224, the pair of pivotal pins can be respectively engaged into two holes 224a formed respectively in the two lugs 224, such that a pivotal axis, around which the locking component 223 is pivotable relative to the outer cover 220, especially the lugs 224, can be defined.

Further as shown by FIGS. 5A to 6B, an installation space can be defined between the lockable portion 223a and the outer cover 220, whose volume can change with the pivoting of the locking component 223. Installed in the installation space can be a force exerting element, for example a torsional spring 226. The torsional spring 226 can be provided with a spiral spring segment and two spring arms 226a and 226b extending from both ends of the spiral spring segment respectively. In a preferred embodiment, the spiral spring segment is coaxial with or is parallel to the pivotal axis of the locking component 223. For instance, the torsional spring 226 can be installed in such a way that the spring arm 226a is in contact with the locking component 223, especially its lockable portion 223a, and the spring arm 226b is in contact with the outer cover 220, especially the side of the outer cover 220 facing the housing base 210.

The actuatable portion 223b of the locking component 223 is located at the side of the outer cover 220 departing from the housing base 210, such that a user can readily touch the actuatable portion 223b via his/her finger and enable the same to be pivoted around the pivotal axis. The torsional spring 226 as the force exerting element is arranged in the installation space between the lockable portion 223a and the outer cover 220 such that no matter how the volume of the installation space changes, a force is always exerted to the lockable portion 223a and the outer cover 220, tending to separate them from each other around the pivotal axis. Therefore, as shown by FIGS. 4A to 4D, after assembled in place, the locking component 223 is pivotable relative to the outer cover 220 between a locking position (FIG. 4A) and an unlocking position (FIGS. 4B and 4C). In the locking position, the actuatable portion 223b is in at least partial contact with the outer cover 220, the volume of the installation space between the lockable portion 223a and the outer cover 220 can reach its maximum, and in the meanwhile the force exerted by the torsional spring 226 between the lockable portion 223b and the outer cover 220 and tending to separate them from each other around the pivotal axis reaches its minimum. In the unlocking position, the actuatable portion 223b is separated from the outer cover 220 to an extreme, the volume of the installation space between the lockable portion 223a and the outer cover 220 can reach its minimum, and in the meanwhile the force exerted by the torsional spring 226 between the lockable portion 223b and the outer cover 220 and tending to separate them from each other around the pivotal axis reaches its maximum.

Two arc-shaped edges 231 are formed on two opposing sidewalls of the lockable portion 223a respectively. A distance between the opposing sidewalls, on which the arc-shaped edges 231 are formed, of the lockable portion 223a is less than or equal to a distance between the arc-shaped ridges 213b of the locking receptacle 213, such that when the lockable portion 223a is located in the locking receptacle 213, each arc-shaped edge 231 is pivotable radially outwards outside the respective arc-shaped ridge 213b as the locking component 230 is pivoted around the pivotal axis. Therefore, the arc-shaped edges 231 can be configured to extend substantially following the trajectory shape of the arc-shaped ridges 213b. The arc-shaped edges 231 and the arc-shaped ridges 213b can overlap at least partially with each other along the thickness direction of the housing base 210.

Figure 4A:
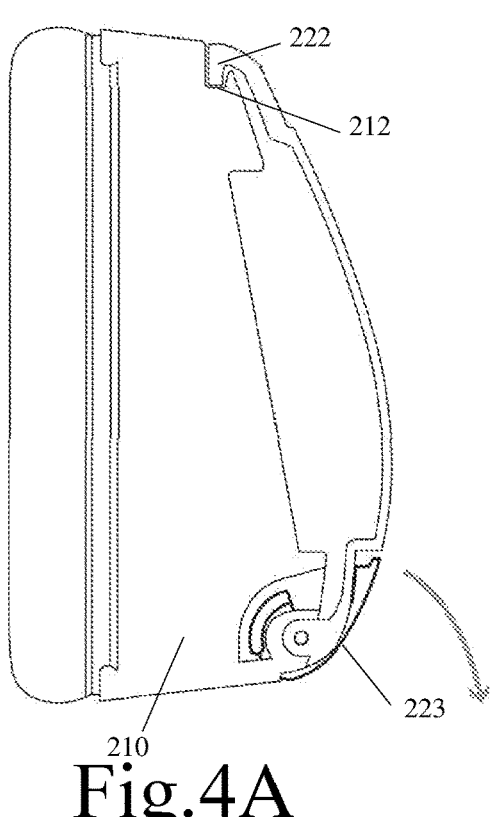
FIGS. 4A to 4D are lateral views schematically illustrating how the outer cover of the ear muff can be unlocked and detached from the base of the housing.
Figure 4B:
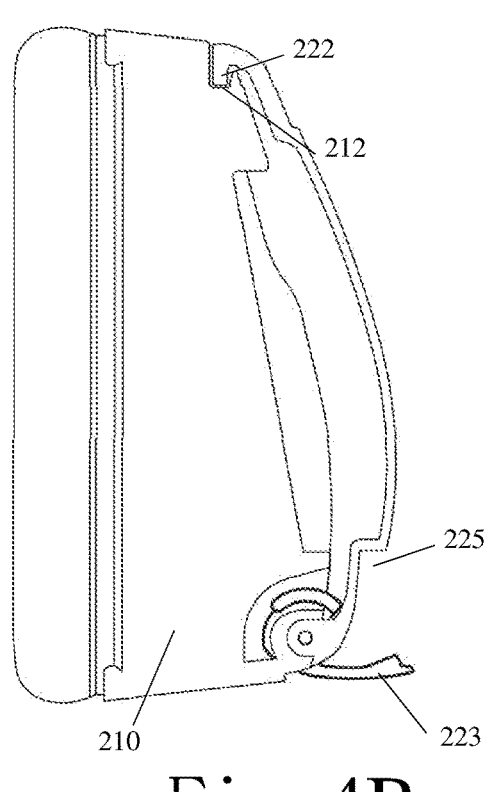
Figure 4C:
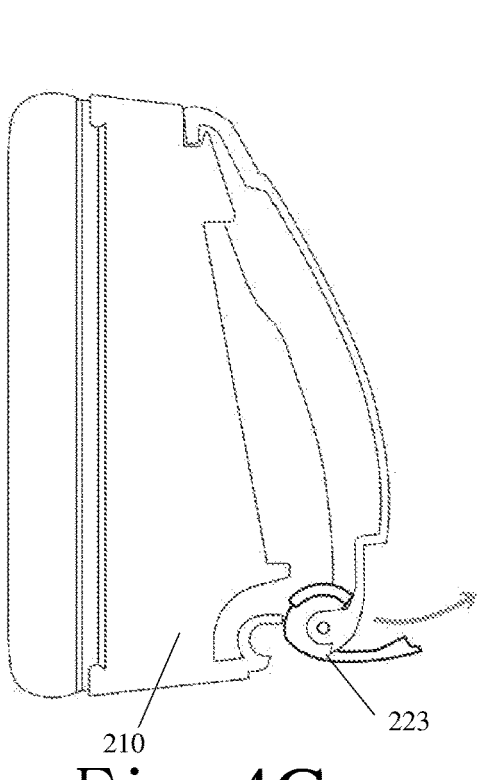
Figure 4D:
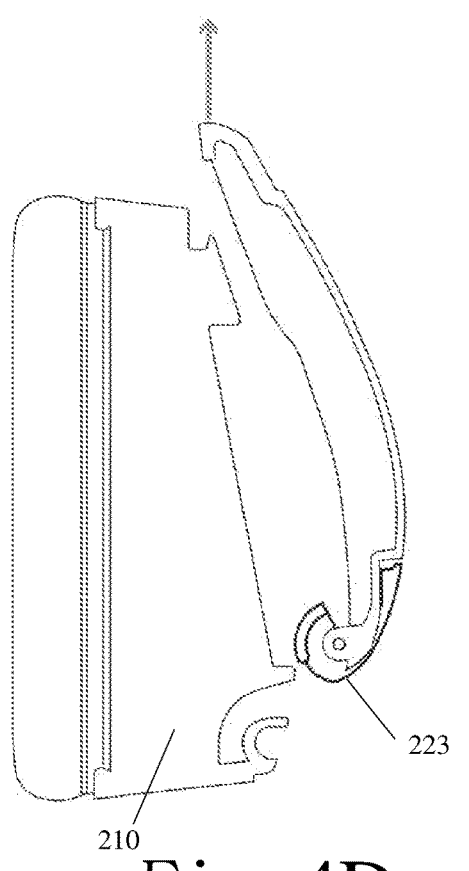
Figure 5A:
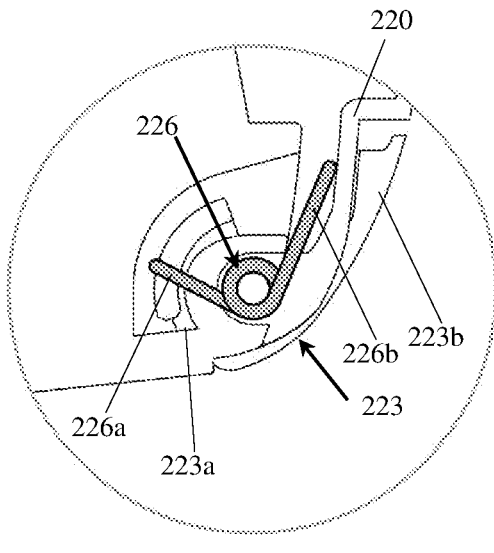
FIG. 5A is a partial view schematically illustrating that a resilient element is configured to act on the locking structure when it is in the locked state.
Figure 5B:
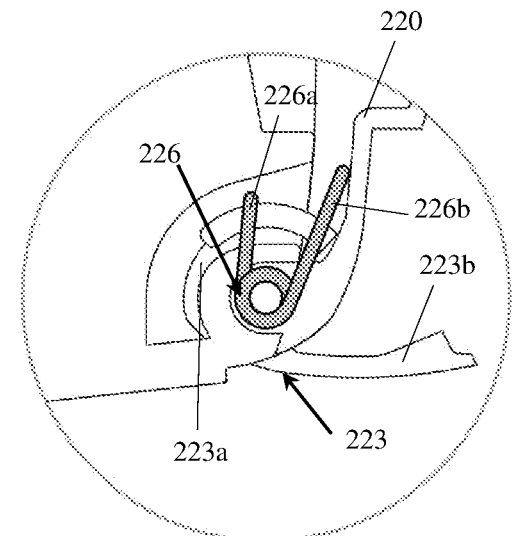
FIG. 5B is a partial view schematically illustrating that the resilient element is configured to act on the locking structure when it is in the unlocked state.

When the locking component 223 is located in the locking receptacle 213 in the locking position as shown by FIG. 4A, the overlap ratio of the arc-shaped edges 231 and the arc-shaped ridges 213b reaches its maximum. At this time, because the arc-shaped edges 231 are obstructed by the arc-shaped ridges 213b, the locking component 223 in the locking receptacle 213 is prevented from at least moving outwards along the thickness direction of the housing base 210. When the locking component 223 is located in the locking receptacle 213 in the unlocking position as shown by FIG. 4B, the overlap ratio of the arc-shaped edges 231 and the arc-shaped ridges 213b reaches its minimum. At this time, at least along the thickness direction of the housing base 210, the arc-shaped edges 231 are no longer obstructed by the arc-shaped ridges 213b such that a user can readily remove the locking component 223 from the locking receptacle 213.

According to an example of the present application, the pivotable locking component 223 (for example as a second locking component) and the projection 222 (for example as a first locking component) which have been already explained can be regarded to substantially constitute a locking structure acting between the outer cover 220 and the housing base 210. Moreover, the locking structure is equipped with the torsional spring 226 as the force exerting element and acting on the locking component 223.

How to install the outer cover 220, equipped with the locking structure, onto the housing base 210 and release the former from the latter will be explained with regard to FIGS. 4A to 4D.

As shown by FIG. 4A, the outer cover 220 is locked in place on the housing base 210. At this time, because of cooperation of the projection 222 with the housing base 210, especially its slot 212 and because of the locking component 223 in the locking position being prevented from being removed from the locking receptacle 213 of the housing base 210, a reliable locking can be achieved between the outer cover 220 and the housing base 210. In order to detach the outer cover 220 from the housing base 210, a user will pull the exposed actuatable portion 223b of the locking component 223 via his/her finger (not shown) such that the locking component 223 can be switched from the locking position to the unlocking position around the pivotal axis, as shown by FIG. 4B. In FIG. 4B, the arc-shaped edges 231, which cannot be seen externally, will not be obstructed by the arc-shaped ridges 213b at least along the thickness direction of the housing base 210. Therefore, the user will be able to pivot the locking component outwards with the projection 222 being the pivotal point, such that the locking component 223 is able to leave the locking receptacle 213, as shown by FIG. 4C. Furthermore, the projection 222 can be moved out of the slot 212 such that the outer cover 220 is separated from the housing base 210. It can be seen from FIGS. 4C and 4D that after or as the finger (not shown) of the user leaves the actuatable portion 223b, the locking component 223 can be automatically returned to its locking position due to the existence of the force exerted by the torsional spring 226 as the force exerting element. In the locking position, the actuatable portion 223b can be fitly located in the recessed section 225 on the outer side of the outer cover 220 such that it looks clean and tidy.

According to the locking structure of the present application, as its locking component 223 requires to be pivoted so as to be switchable between the locking position and the unlocking position, it will be more convenient for a user to operate the locking structure. For instance, on a bad engineering site, it will be avoided that dirt or sweat on the user's finger let the locking component be movable difficult. Otherwise, if the locking component were designed to be linearly movable, what would most likely happen were that the component will be moved difficultly. Furthermore, as the direction along which the locking component 223 is pivoted for locking or unlocking and the direction along which the outer cover is detached are completely not coplanar or parallel to each other, the outer cover can be locked to the housing base with higher reliability. More importantly, because the force exerting element is adopted in the locking component 223, a force always exists to ensure that the locking component 223 can be returned to its locking position or it can be reliably held to the locking position. Therefore, in comparison with a case in which no force exerting element is adopted, the present application greatly decreases the possibility of accidental failure of the locking structure.

Figure 6A:
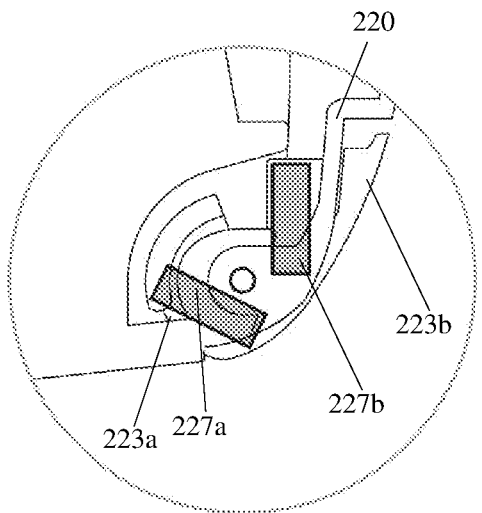
FIG. 6A is a partial view schematically illustrating an ear muff according to another embodiment of the present application, wherein a force exerting element is configured to act on a locking structure when it is in a locking state.
Figure 6B:
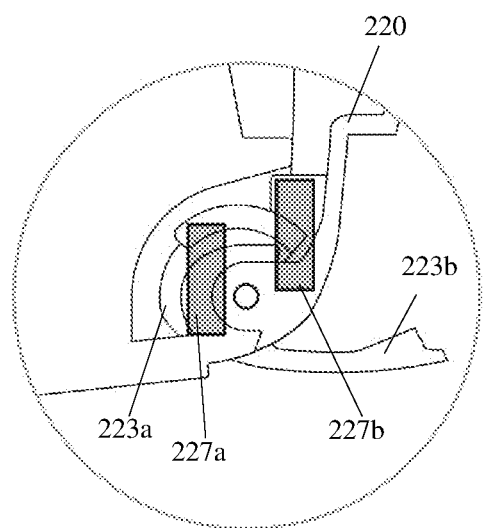
FIG. 6B is a partial view schematically illustrating the earmuff according to the anther embodiment of the present application, wherein the force exerting element is configured to act on the locking structure when it is in an unlocking state.

According to an alternative embodiment of the present application, as shown by FIGS. 6A and 6B, the force exerting element provided between the locking component 223 and the outer cover 220 can be in the form of a pair of magnets 227*a*, 227*b*. For instance, in the installation space which is defined between the lockable portion 223*a* and the outer cover 220 and whose volume changes as the locking component 223 is pivoted around the pivotal axis, the magnet 227*a* can be disposed on the locking component 223 for example the lockable portion 223*a*, and the magnet 227*b* can be disposed on a side of the outer cover 220 facing the lockable portion 223*a*. Moreover, a side of the magnet 227*a* and a side of the magnet 227*b* opposing each other have the same magnetism. Therefore, because of repulsion between the two magnets caused by the same magnetism, a force always exists which tends to enable the locking component 223 to be pivoted relative to the outer cover 220 around the pivotal axis and thus to separate them from each other around the pivotal axis. In the meanwhile, the force will increase as the volume of the installation space decreases. That is to say, in the locking position as shown by FIG. 6A, the actuatable portion 223*b* is in at least partial contact with the outer cover 220, the volume of the installation space between the actuatable portion 223*b* and the outer cover 220 reaches its maximum, and the repulsive force exerted by the magnets 227*a*, 227*b* between the actuatable portion 223*a* and the outer cover 220 reaches its minimum. In the unlocking position, the actuatable portion 223*b* is separated from the outer cover 220 to an extreme, the volume of the installation space between the actuatable portion 223*b* and the outer cover 220 reaches its minimum, and in the meanwhile the repulsive force exerted by the magnets 227*a*, 227*b* between the actuatable portion 223*a* and the outer cover 220 reaches its maximum.

In an alternative embodiment not shown, the force exerting element can be in the form of a U-shaped leaf spring located in the installation space which is defined between the lockable portion 223*a* and the outer cover 220 and whose volume changes as the locking component 223 is pivoted around the pivotal axis, such that as the volume of the installation space changes, a distance between two wings of the U-shaped leaf spring which are in respective contact with the locking component 223 and the outer cover 220 also changes. Using the U-shaped leaf spring, a force can be applied between the locking component and the outer cover, tending to separate them from each other around the pivotal axis. However, it should be understood by a person skilled in the art that the already described embodiments are given out for non-limited purposes only; and any type of force exerting element can be adopted in the present application as long as the force exerting element can apply a force between two relatively pivotable components, tending to separate them from each other around the pivotal axis. Such a force exerting element is designed in such a way that without any other external force, the locking component 223 can be automatically returned from the unlocking position to the locking position.

In an embodiment of the present application, the arc-shaped ridges 213*b* and the arc-shaped edges 231 can be embodied in pairs. However, it should be understood by a person skilled in the art that in an alternative embodiment only a single arc-shaped ridge 213*b* and a single arc-shaped edge 231 cooperating with the same can be provided. Alternatively, more arc-shaped ridges and more arc-shaped edges can be provided as desired. Furthermore, one of the arc-shaped ridge 213*b* and the arc-shaped edge 231 can be in the form of non-arc, for example embodied as a block as long as it can be used to ensure that in the locking position of the locking component 223, the locking component 223 can be locked in place in the locking receptacle 213 due to resistance action therebetween. Even in an alternative embodiment, a claw can be provided in the lockable portion 223*a* of the locking component 223 and a receiver can be provided in the locking receptacle 213 to receive the claw such that cooperation of the claw with the receive enables the locking component 223 to be locked in the locking receptacle 213. For instance, in this case, the claw is configured to engage the receiver in the locking position of the locking component 223, such that the locking component 223 can be locked in place in the locking receptacle 213. Of course, it should be understood by a person in the art that in this design the claw and the receiver can be swapped their places between the locking component 213 and the outer cover 220.

Although some specific embodiments of the present application have been described here, they are given for illustrative purposes only and cannot be construed to constrain the scope of the present application in any way. Furthermore, it should be understood by a person skilled in the art that the embodiments/examples described here can be arbitrarily combined with each other. Without departing from the spirit and scope of the present application, various modifications, replacements, and alternations can be thought out.

The invention claimed is:

1. An ear muff comprising:
   a housing base in which an acoustic cavity for noise attenuation is formed and a chamber for receiving an electronic device is formed;
   an outer cover for at least covering the chamber; and
   a locking structure acting between the outer cover and the housing base, so as to achieve a releasable connection between the outer cover and the housing base, characterized in that the locking structure comprises:
   a first locking component securely provided on the outer cover to selectively engage the housing base;
   a second locking component pivotably provided on the outer cover and spaced apart from the first locking component, the second locking component comprising a lockable portion and an actuatable portion and configured to be pivotable between a locking position, in which the outer cover is able to be locked together with the housing base due to the locking structure, and an unlocking position in which the outer cover is able to be released from the housing base, wherein actuating the actuatable portion causes circular rotation of the lockable portion toward the unlocking position; and
   a force exerting element provided between the second locking component and the outer cover by which force exerting element a force is always applied to the second locking component, tending to return the second locking component from the unlocking position to the locking position,
   wherein when the second locking component is in the locking position, the lockable portion is at least partially disposed within the housing base and the actuatable portion is in contact with an outer surface of the outer cover.

2. The ear muff as recited in claim 1, wherein the first locking component is configured to engage both of the second locking component in its locking position and the housing base so as to lock the outer cover to the housing base.

3. The ear muff as recited in claim 1, wherein the force exerting element is located in an installation space which is defined between the second locking component and the outer cover and whose volume is able to change as the second locking component is pivoted.

4. The ear muff as recited in claim 2, wherein the force exerting element is located in an installation space which is defined between the second locking component and the outer cover and whose volume is able to change as the second locking component is pivoted.

5. The ear muff as recited in claim 3, wherein the first locking component comprises or is a projection formed on a circumferentially extending edge of the outer cover, and a slot is formed in a peripheral region of the housing base to engage the projection.

6. The ear muff as recited in claim 4, wherein the first locking component comprises or is a projection formed on a circumferentially extending edge of the outer cover, and a slot is formed in a peripheral region of the housing base to engage the projection.

7. The ear muff as recited in claim 5, wherein a locking receptacle is formed in the peripheral region of the housing base to at least partially receive the second locking component.

8. The ear muff as recited in claim 6, wherein a locking receptacle is formed in the peripheral region of the housing base to at least partially receive the second locking component.

9. The ear muff as recited in claim 7, wherein the first locking component is spaced apart from the second locking component along a diameter of the outer cover.

10. The ear muff as recited in claim 8, wherein the first locking component is spaced apart from the second locking component along a diameter of the outer cover.

11. The ear muff as recited in claim 9, wherein the lockable portion is configured together with the outer cover to define the installation space, and wherein when the outer cover is locked to the housing base, the lockable portion is at least partially located in the locking receptacle and the actuatable portion is exposed.

12. The ear muff as recited in claim 10, wherein the lockable portion is configured together with the outer cover to define the installation space, and wherein when the outer cover is locked to the housing base, the lockable portion is at least partially located in the locking receptacle and the actuatable portion is exposed.

13. The ear muff as recited in claim 11, wherein the lockable portion comprises at least an arc-shaped edge, at least one arc-shaped ridge is formed in the locking receptacle, the arc-shaped edge is formed to follow the arc-shaped ridge such that when the lockable portion is pivoted in the locking receptacle, the arc-shaped edge is pivoted around the arc-shaped ridge.

14. The ear muff as recited in claim 13, wherein the arc-shaped edge is configured to in the locking position apply a force to the arc-shaped ridge so as to resist the lockable portion leaving the locking receptacle.

15. The ear muff as recited in claim 14, wherein the force exerting element is configured as a torsional spring which is provided with a spiral spring segment and two spring arms extending from both ends of the spiral spring segment respectively.

16. The ear muff as recited in claim 15, wherein in the installation space, one of the two spring arms is in contact with the second locking component and the other is in contact with the outer cover.

17. The ear muff as recited in claim 14, wherein the force exerting element is configured as a pair of magnets, a first magnet of the pair of magnets is located on the lockable portion and a second magnet of the pair of magnets is located on the outer cover, and a side of the first magnet and a side of the second magnet opposing each other have the same magnetism.

18. The ear muff as recited in claim 1, wherein the electronic device comprises an electronic device for noise attenuation.

19. The ear muff as recited in claim 2, wherein the electronic device comprises an electronic device for noise attenuation.

20. An ear muff assembly comprising:

a headband; and a pair of ear muffs which are releasably connected to opposing ends of the headband respectively, wherein one or each ear muff of the pair of car muffs includes:

a housing base in which an acoustic cavity for noise attenuation is formed and a chamber for receiving an electronic device is formed;

an outer cover for at least covering the chamber; and a locking structure acting between the outer cover and the housing base, so as to achieve a releasable connection between the outer cover and the housing base, characterized in that the locking structure comprises:

a first locking component securely provided on the outer cover to selectively engage the housing base;

a second locking component pivotably provided on the outer cover and spaced apart from the first locking component, the second locking component comprising a lockable portion and an actuatable portion and configured to be pivotable between a locking position, in which the outer cover is able to be locked together with the housing base due to the locking structure, and an unlocking position in which the outer cover is able to be released from the housing base, wherein actuating the actuatable portion causes circular rotation of the lockable portion toward the unlocking position; and a force exerting element provided between the second locking component and the outer cover by which force exerting element a force is always applied to the second locking component, tending to return the second locking component from the unlocking position to the locking position wherein when the second locking component is in the locking position, the lockable portion is at least partially disposed within the housing base and the actuatable portion is in contact with an outer surface of the outer cover.

* * * * *